(12) United States Patent
Floquet et al.

(10) Patent No.: US 9,025,152 B2
(45) Date of Patent: May 5, 2015

(54) MICROFLUIDIC ABSORPTION CELL

(75) Inventors: Cedric Florian Aymeric Floquet, Edmonton (CA); Hywel Morgan, Southampton (GB); Vincent Joseph Sieben, Edmonton (CA); Iain Rodney George Ogilvie, Southampton (GB); Matthew Charles Mowlem, Emsworth (GB)

(73) Assignee: University of Southampton, Hampshire (GB)

( * ) Notice: Subject to any disclaimer, the term of this patent is extended or adjusted under 35 U.S.C. 154(b) by 218 days.

(21) Appl. No.: 13/805,806

(22) PCT Filed: Feb. 4, 2011

(86) PCT No.: PCT/GB2011/050198
§ 371 (c)(1),
(2), (4) Date: Dec. 20, 2012

(87) PCT Pub. No.: WO2011/095821
PCT Pub. Date: Aug. 11, 2011

(65) Prior Publication Data
US 2014/0176952 A1    Jun. 26, 2014

(30) Foreign Application Priority Data

Feb. 4, 2010 (GB) .................................. 1001886.9

(51) Int. Cl.
*G01N 21/17* (2006.01)
*B01L 3/00* (2006.01)
(Continued)

(52) U.S. Cl.
CPC .......... *G01N 21/17* (2013.01); *B01L 3/502715* (2013.01); *B01L 2300/0654* (2013.01); *B01L 2300/0816* (2013.01); *B01L 2300/12* (2013.01); *G01N 21/0303* (2013.01);
(Continued)

(58) Field of Classification Search
USPC .................. 356/244, 246, 432–440, 317, 326
See application file for complete search history.

(56) References Cited

U.S. PATENT DOCUMENTS 4,810,096 A  * 3/1989 Russell et al. ................. 356/436
5,444,807 A    8/1995 Liu
(Continued)

FOREIGN PATENT DOCUMENTS

DE    20 2008 010860    10/2008
WO       03/073069       9/2003

OTHER PUBLICATIONS

Adornato et al., "Continuous in situ determinations of nitrite at nanomolar concentrations", Deep-Sea Research I 52, 2005, pp. 543-551.
(Continued)

*Primary Examiner* — Hoa Pham
(74) *Attorney, Agent, or Firm* — Renner, Otto, Boisselle & Sklar, LLP

(57) ABSTRACT

An absorption cell for microfluidic chemical analysis made from tinted or colored polymers, for example polymethylmethacrylate (PMMA), in which microfluidic channels are cut. Light is coupled into the absorption cell via two windows (typically 200 um thick) that are retained at either end of the channel. Absorption is measured using a light source, such as a light emitting diode (LED) and a photodiode butted against the windows. Spurious scattered and/or reflected light is absorbed by the colored polymer over the length of the measurement cell, while very little light loss occurs at the coupling windows.

12 Claims, 7 Drawing Sheets

(51) Int. Cl.
  *G01N 21/03* (2006.01)
  *G01N 21/05* (2006.01)
(52) U.S. Cl.
  CPC ....... *G01N 21/05* (2013.01); *G01N 2021/0346* (2013.01); *G01N 2021/0389* (2013.01); *G01N 2201/064* (2013.01)

(56) References Cited

U.S. PATENT DOCUMENTS

| | | | | |
|---|---|---|---|---|
| 6,048,498 | A * | 4/2000 | Kennedy | 422/503 |
| 7,952,705 | B2 * | 5/2011 | Shen et al. | 356/246 |

OTHER PUBLICATIONS

Armstrong et al, "The measurement of upwelling and subsequent biological processes by means of the Technicon Autoanalyzer and associated equipment", Deep-Sea Research, 1967, vol. 14, pp. 381-389.
Beer, Annalen der Physik, 1852, pp. 67-79.
Billot et al., "Multi-reflection based on chip label free molecules detection", Microelectronic Engineering 85, 2008, pp. 1269-1271.
Bliss et al., "Integrated wavelength-selective optical waveguides for microfluidic-based laser-induced fluorescence detection", Lab Chip, © The Royal Society of Chemistry, 2008, pp. 143-151.
Brasseur et al., "Integrating Biogeochemistry and Ecology Into Ocean Data Assimilation Systems", Oceanography vol. 22, No. 3, 2009, pp. 206-215.
Chin et al., "Spectrophotometric determination of dissolved manganese in natural waters with 1-(2-pyridylazo)-2-naphthol: application to analysis in situ in hydrothermal plumes", Marine Chemistry, 37, 1992, pp. 65-82.
Chin et al., "In situ observations of dissolved iron and manganese in hydrothermal vent plumes, Juan de Fuca Ridge", Journal of Geophysical Research, vol. 99, No. B3, Mar. 10, 1994, pp. 4969-4984.
Datta et al., "Microfabrication and Characterization of Teflon AF-Coated Liquid Core Waveguide Channels in Silicon", IEEE Sensors Journal, vol. 3, No. 6, Dec. 2003, pp. 788-795.
Delworth et al., "GFDL's CM2 Global Coupled Climate Models. Part I: Formulation and Simulation Characteristics", American Meteorological Society, Journal of Climate, Mar. 1, 2006, pp. 643-674.
Dickson et al., "Guide to best practices for ocean CO2 measurements", PICES Special Publication 3, 2007.
Dittrich et al., "Micro Total Analysis Systems. Latest Advancements and Trends", Analytical Chemistry, vol. 78, No. 12, Jun. 15, 2006, pp. 3887-3908.
Ducklow et al., "Contributions of Long-Term Research and Time-Series Observations to Marine Ecology and Biogeochemistry", Annual Review of Marine Science, 2009, pp. 279-302.
Duggan et al., "A non-invasive analysis method for on-chip spectrophotometric detection using liquid-core waveguiding within a 3D architecture", The Analyst, The Royal Society of Chemistry, 2003, pp. 1336-1340.
Friedrichs et al., "Assessment of skill and portability in regional marine biogeochemical models: Role of multiple planktonic groups", Journal of Geophysical Research, vol. 112, 2007, pp. 1-22.
C. Galli, "Modeling systematic errors: polychromatic sources of Beer-Lambert deviations in HPLC/UV and nonchromatographic spectrophotometric assays", Journal of Pharmaceutical and Biomedical Analysis, 2001, pp. 803-809.
Greenway et al., "Characterisation of a micro-total analytical system for the determination of nitrite with spectrophotometric detection", Analytica Chimica Acta 387, 1999, pp. 1-10.
Peter Griess, Berichte der deutschen chemischen Gesellschaft, Mar. 1879, pp. 426-428.
Grumann et al., "Sensitivity enhancement for colorimetric glucose assays on whole blood by on-chip beam-guidance", Biomed Microdevices, ©Springer Science + Business Media, May 27, 2006, pp. 209-214.
Alfred K. Hanson, "A New In Situ Chemical Analyzer for Mapping Coastal Nutrient Distributions in Real Time", IEEE, 2000, pp. 1975-1982.
Hofmann et al., "Monolithically integrated dye-doped PDMS long-pass filters for disposable on-chip fluorescence detection", Lab Chip, © The Royal Society of Chemistry, 2006, pp. 981-987.
Hood et al., "A four-dimensional validation of a coupled physical-biological model of the Arabian Sea", Deep-Sea Research II 50, 2003, pp. 2917-2945.
Hunt et al., "Optofluidic integration for microanalysis", Microfluid Nanofluid, 2008, pp. 53-79.
Johnson et al., "Observing biogeochemical cycles at global scales with profiling floats and gliders: Prospects for a global array", Oceanography vol. 22, No. 3, 2009, pp. 216-225.
Kuswandi et al., "Optical sensing systems for microfluidic devices: A review", Analytica Chimica Acta 601, 2007, pp. 141-155.
Kyung Won Ro et al., "Integrated Light Collimating System for Extended Optical-Path-Length Absorbance Detection in Microchip-Based Capillary Electrophoresis", Analytical Chemistry, vol. 77, No. 16, Aug. 15, 2005, pp. 5160-5166.
Li et al., "Applications of microfluidic systems in environmental analysis", Analytical Bioanalytical Chemistry, 2009, pp. 555-567.
Liang et al., "Microfabrication of a Planar Absorbance and Fluorescence Cell for Integrated Capillary Electrophoresis Devices", Analytical Chemistry, vol. 68, No. 6, Mar. 15, 1996, pp. 1040-1046.
Manor et al., "Microfabrication and Characterization of Liquid Core Waveguide Glass Channels Coated with Teflon AF", IEEE Sensors Journal, vol. 3, No. 6, Dec. 2003, pp. 687-692.
Manz et al., "Miniaturized Total Chemical Analysis Systems: a Novel Concept for Chemical Sensing", Sensors and Actuators, B1, 1990, pp. 244-248.
Marle et al., "Microfluidic devices for environmental monitoring", Trends in Analytical Chemistry, vol. 24, No. 9, 2005, pp. 795-802.
Pandraud et al., "Evanescent wave sensing: new features for detection in small volumes", Sensors and Actuators 85, 2000, pp. 158-162.
Patey et al., "Determination of nitrate and phosphate in seawater at nanomolar concentrations", Trends in Analytical Chemistry, vol. 27, No. 2, 2008, pp. 169-182.
Remley et al., "Design and analysis of a silicon-based antiresonant reflecting optical waveguide chemical sensor", Optics Letters, vol. 21, No. 16, Aug. 15, 1996, pp. 1241-1243.
Salimi-Moosavi et al., "A multireflection cell for enhanced absorbance detection in microchip-based capillary electrophoresis devices", Electrophoresis, vol. 21, 2000, pp. 1291-1299.
Lawrence L. Stookey, "Ferrozine—A New Spectrophotometric Reagent for Iron", Analytical Chemistry, vol. 42, No. 7, Jun. 1970, pp. 779-781.
Thouron et al., "An Autonomous Nutrient Analyzer for Oceanic Long-Term in Situ Biogeochemical Monitoring", Analytical Chemistry, vol. 75, 2003, pp. 2601-2609.
Tsao et al., "Bonding of thermoplastic polymer microfluidics", Microfluid Nanofluid, vol. 6, pp. 1-16.
Du et al., "High-Throughput Nanoliter Sample Introduction Microfluidic Chip-Based Flow Injection Analysis System with Gravity-Driven Flows", Analytical Chemistry, vol. 77, 2005, pp. 1330-1337.
Zhang et al., "Spectrophotometric pH measurements of surface seawater at in-situ conditions: absorbance and protonation behavior of thymol blue", Marine Chemistry 52, 1996, pp. 17-25.
International Search Report for corresponding patent application No. PCT/GB2011/0550198 dated Apr. 27, 2011.
Written Opinion for corresponding patent application No. PCT/GB2011/0550198 dated Apr. 27, 2011.
International Preliminary Report on Patentability for corresponding patent application No. PCT/GB2011/0550198 dated Aug. 7, 2012.

* cited by examiner

MICROFLUIDIC ABSORPTION CELL

This application is a national phase of International Application No. PCT/GB2011/050198 filed Feb. 4, 2011 and published in the English language.

BACKGROUND OF THE INVENTION

The invention relates to absorption cells for microfluidic chemical analysis.

Microfluidic lab-on-a-chip (LOC) platforms[1,2] show considerable promise for the creation of robust miniaturised, high performance metrology systems with applications in diverse fields such as environmental analysis[3,4], potable and waste water, point of care diagnostics and many other physical, chemical and biological analyses. The technology allows the integration of many components and subsystems (e.g. fluidic control, mixers, lenses, light sources and detectors) in small footprint devices that could potentially be mass produced. Reduction in size enables reduction in power and reagent consumption making miniaturisation of a complete sensing system feasible. There are many applications to this technology, particularly in the development of remote in situ sensing systems for environmental analysis, and one area of importance is the measurement of ocean biogeochemistry.

Long term, coherent and synoptic observations of biogeochemical processes are of critical relevance for interpretation and prediction of the oceans' (and hence the earth's) response to elevated $CO_2$ concentrations and climate change. Observations of oceanographic biogeochemical parameters are used to constrain biogeochemical models and understanding[5-7] that in turn informs modelling of the ocean[8] and earth system[9]. A promising approach for obtaining oceanographic biogeochemical data on enhanced spatial and temporal scales is to add biogeochemical sensors to existing networks of profiling floats or vehicles[10]. For long-term deployments these sensors should have high resolution and accuracy, negligible buoyancy change, low consumption of power and/or chemical reagents, and be physically small.

Colourimetric assays for determination of inorganic chemical concentrations (e.g. Nitrate/Nitrite[11], Phosphate[12], Iron[13] and Manganese[14] have long providence and are used widely in oceanography. Applied in laboratory[15], shipboard[16], and in situ analysis[17-19] (i.e. in a submerged analytical system) they enable measurements over a wide measurement range including at low open ocean concentrations[20].

The performance of colourimetric analytical systems is determined by both the fluidic and optical sub-systems. The optical system consists of an opto-fluidic cell in which the absorption of a fixed length of fluid is determined. The idealised relationship between the measured optical power, absorbance and chemical concentration is described by the Bouguer-Beer-Lambert law[21-23]. For mathematical simplicity we present here the exponential form of Beer's law[23].

$$P_{sample} = P_0 e^{-\alpha cl} \quad \text{Equation 1}$$

Where $P_{sample}$ is the measured optical power, $P_0$ the power of the optical source, $\alpha$ the absorption coefficient of the absorbing species, c the concentration of the absorbing species and l the effective length of the absorption cell. Care must also be taken in using the correct values of extinction coefficient from the literature as both natural and common logarithmic versions of the Bouguer-Beer-Lambert law are used.

The Bouguer-Beer-Lambert law only applies if a monochromatic light source is used, and if the concentration is low enough so that there is no interaction between molecules of the absorbing species. In this case, the absorbance due to the presence of the analyte and hence the concentration, is determined using Equation 2

$$A = \alpha cl = \ln \frac{P_{ref}}{P_{sample}} \quad \text{Equation 2}$$

$P_{ref}$ is frequently determined by measurement of a blank (i.e. a sample with no absorbing species)

The sensitivity of an idealised optical cell is maximum when the absorbance is equal to unity which implies an optimal cell length for a given absorption coefficient and concentration, which is determined as follows:

$$\frac{d\left(\frac{dP_{sample}}{dC}\right)}{dl} = -\alpha^2 l c P_0 e^{(-\alpha lc)} + \alpha P_0 e^{(-\alpha lc)} \quad \text{Equation 3}$$

and at maximal sensitivity $$\frac{d\left(\frac{dP_{sample}}{dC}\right)}{dl} = 0 \rightarrow \alpha = \alpha^2 lc \rightarrow \alpha lc = 1$$

In practical implementations, monochromatic light is not used and $P_0$ and $\alpha$ are wavelength dependent. In addition, ambient and stray light can arrive at the detector causing an offset; this light is unaffected by the concentration of the analyte. Therefore the measured power is $$P = \int P_0(\lambda) e^{-\alpha(\lambda)cl} d\lambda + P_{offset} \quad \text{Equation 4}$$

The spectral characteristics of the source and the extinction coefficient (even in the absence of stray light) imply that Equation 2 is not always applicable and if used incorrectly can result in a non-linear absorption measurement. For example Galli[24] developed an analytical solution for a Gaussian source spectrum and a linear slope molecular extinction coefficient spectrum that demonstrates this departure from idealised behaviour.

Neglecting spectral effects, simple (and incorrect) application of Equation 2 without consideration of stray light causes a non-linear relationship between the effective absorption and concentration:

$$A = \ln \frac{P_{ref}}{P_{sample}} = \ln \frac{(P_0 + P_{offset})}{(P_0 e^{-\alpha cl} + P_{offset})} \quad \text{Equation 5}$$

This deviation can be corrected if $P_{offset}$ is known, and this can be determined directly by measuring the optical power when an opaque sample is placed in the absorption cell. A widely accepted method of obtaining high accuracy metrology is to eliminate stray light and to ensure the source, absorption and detector-sensitivity spectra convolve to give a wavelength independent response.

There have been many different approaches to integration and miniaturisation of microfluidic absorption cells. There are many examples of the use of thin and transparent materials to manufacture microchannel absorption cells[25], but this approach is problematic. Whilst opto-fluidic integration with low dead volumes is possible the cell's absorption length is typically short, and stray light degrades performance.

Kuswandi et al.[26] and Hunt and Wilkinson[25] recently reviewed opto-fluidic integration highlighting recent advances, including absorption cell design. Many systems use optical fibres for launching and collecting light from U-shaped (e.g.[27]) or Z shaped channels (e.g.[28]). Whilst the fibres' numerical aperture provides a degree of stray light rejection, alignment can be problematic. Complexity and optical power loss is also caused by coupling between fibres, sources and detectors. Grumann et al.[29] used total internal reflection at an air interface in their polymeric devices to simplify coupling of out of plane sources and detectors to 10 mm long absorption cells. Stray light reduction relied on collimation of the laser source used. Lenses have been used to increase coupling efficiencies and to reduce stray light, but require complex fabrication for relatively short (500 μm) channels[30]. The use of liquid core waveguides (LCWs) enables both long path lengths and stray light rejection[31-34]. However LCWs can require complex fabrication and frequently rely on internal Teflon AF coatings that have poor long term performance (commercial macro Teflon AF based LCWs are supplied with a glass liner to prevent internal degradation). Multiple reflections can be used to increase effective absorption length to greater than the geometric length[35, 36] though alignment and collimation remain problematic and only short effective path lengths are obtained. ARROW waveguide (e.g.[37]) and other structures facilitating absorption detection in the evanescent wave (e.g.[38]) but result in short interaction lengths for a given geometric length. Substrates doped with wavelength selective absorbent dyes that enable spectral filtering have been demonstrated in PDMS[39, 40, 25] for optical filtering in fluorescence based systems. These arrangements have not been used for colourimetric assays and the control of stray light.

Despite these innovations simple, low-cost, robust absorption cells with long path lengths and low stray-light transmission remain elusive.

SUMMARY OF THE INVENTION

A first aspect of the invention provides an absorption cell for measuring absorption of a fluid analyte at a sensing wavelength, or range of sensing wavelengths, by exposing the analyte to probe light of the sensing wavelength or sensing wavelength range, the absorption cell comprising: a microfluidic sensing channel formed in a tinted material which is neither transparent nor opaque to the probe light, but rather transmissive and absorbent to the probe light, and having first and second ends so as to provide a fluid path for the analyte as well as an optical path for the probe light; first and second windows formed in the tinted material integrally with the sensing channel which are sufficiently thin to be transmissive to the probe light and which are arranged adjacent the first and second ends of the sensing channel respectively. It is therefore possible to use a monolithic structure, e.g. made up of two or more blocks of the tinted material which are bonded together to form the cell in a layered structure.

The tinted material can be defined in terms of its optical loss to the probe light, and in embodiments of the invention can be at least 10, 20 or 30 90 dB/cm, e.g. between 10 to 90 dB/cm, or 20 to 90, or 30 to 90. In specific examples, the optical loss is 32.9 and 88.9 dB/cm. The technique will also work with much higher optical losses, especially if the windows are very thin. For example a 1000 dB/cm material with a 50 μm window thickness will result in an acceptable 5 dB loss of probe light at each window.

The use of tinted material and integral windows of the tinted material allows the sensing channel to be made very long, for example the length of the sensing channel can be at least 10 mm, at least 25 mm, or at least 80 mm. The length of the sensing channel may be defined, for example, by the distance between the first and second windows. Much longer lengths of sensing channel are possible, e.g. 1 m.

The ratio of the length of the sensing channel to the combined thickness of the first and second windows is a useful measure of the trade off between allowing sufficient probe light into and out of the cell for an acceptable signal-to-noise ratio, and obtaining sufficient extinction of stray probe light or other stray light derived from scattering of the probe light before it reaches the second window, i.e. the photodetector. The ratio of the length of the sensing channel to the combined thickness of the first and second windows is preferably greater than or equal to 50, in the range 50 to 125, or 50 to 160, or 50 to 400. Even a value of 10 or more will provide sufficient stray light suppression for some applications. Specific examples may have values of $10^4$ or more, for example with sensing channel lengths in the meter range.

In embodiments of the invention, the transmission of the probe light in the tinted material over a path length equal to the combined thickness of the first and second windows is between 30% and 90%, or 30% and 80%. In specific examples, the transmission is 35.9%, 66.4%, 68.5% or 85.9%. This compares to the transmission through transparent windows which is typically greater than 95%, e.g. 98.6% or 99.4%. The windows may therefore be described as semi-transparent to the probe light.

In embodiments of the invention, good extinction of the stray probe light, or other scattered light derived from the probe light, can be achieved by ensuring that the transmission of the probe light in the tinted material over a path length equal to the length of the sensing channel is sufficiently small, for example less than $10^{-6}$. The transmission of the probe light in the tinted material over a path length equal to the length of the sensing channel could be less than $10^{-7}$, $10^{-10}$ or $10^{-20}$. Specific examples have transmissions of $6.0 \times 10^{-7}$, $6.0 \times 10^{-21}$ and $7.6 \times 10^{-70}$. The technique will function so long as the transmission values are lower than about $10^{-2}$ and with some specific examples the transmission values may be as small as $10^{-1000}$.

The ratio of the transmission of the probe light in the tinted material over a path length equal to the combined thickness of the first and second windows, and the transmission of the probe light in the tinted material over a path length equal to the length of the sensing channel is another useful measure of the trade off between allowing sufficient probe light into and out of the cell for an acceptable signal-to-noise ratio, and obtaining sufficient extinction of stray probe light or other stray light derived from scattering of the probe light before it reaches the second window. For example, the ratio may be at least $10^8$, or in the range $10^8$ to $10^{70}$ in some embodiments. By comparison, with a cell in which the substrate and windows are made of transparent polymer material the ratio is likely to be in the range 3 or 4 to perhaps 10, i.e. several orders of magnitude lower. The technique will function so long as this ratio is higher than about $10^2$.

The tinted material has a grey colour in some embodiments. In some examples using a grey tint, the tinted material is light grey and in others it is dark grey. A grey colour indicates that the material has significant absorption across the visible wavelengths.

The sensing channel is advantageously connected at its first end by a first elbow to a microfluidic input channel in fluid communication with a fluid input and at its second end by a second elbow to a microfluidic output channel in fluid communication with a fluid output. With a flat sided cell, the elbow will have an obtuse angle, i.e. an angle of between 90 and 180 degrees.

In embodiments of the invention, the first and second windows have first and second internal faces formed at the first and second elbows between the first and second ends of the sensing channel and the input and output channel respectively, and first and second external faces through which probe light is able to couple into and out of the absorption cell respectively.

In one embodiment, the tinted material is a thermoplastic organic polymer. Suitable thermoplastic organic polymers that can be used to provide the substrate include, but are not limited to, polyalkenes (polyolefins), polyamides (nylons), polyesters, polycarbonates, polyimides and mixtures thereof. Any polymer or glass material would function provided it had appropriate absorption properties as well as complying with the liquid handling requirements of the analyte fluid as far as contamination are concerned.

A second aspect of the invention relates to an absorption cell device for measuring absorption of a fluid analyte at a sensing wavelength, or range of sensing wavelengths, by exposing the analyte to probe light of the sensing wavelength or sensing wavelength range, the device comprising: a microfluidic input channel in fluid communication with a fluid input; a microfluidic output channel in fluid communication with a fluid output; a microfluidic sensing channel formed in a tinted material which is neither transparent nor opaque to the probe light, but rather transmissive and absorbent to the probe light, the sensing channel having first and second ends in fluid connection with the input channel and output channel respectively, so as to provide a fluid path for the analyte as well as an optical path for the probe light; first and second windows formed in the tinted material integrally with the sensing channel and arranged adjacent the first and second ends of the sensing channel which are sufficiently thin to be transmissive to the probe light; a light source operable to generate the probe light and arranged to direct the probe light into the optical path through the first window; and a photodetector operable to sense the probe light and arranged to receive the probe light from the optical path through the second window.

In the device, the first and second windows can have first and second internal faces formed at first and second channel elbows between the first and second ends of the sensing channel and the input and output channel respectively, and first and second external faces through which probe light is able to couple into and out of the absorption cell respectively.

A third aspect of the invention relates to a method of performing an absorption measurement of a fluid analyte, the method comprising: providing an absorption cell with a microfluidic sensing channel formed in a tinted material which is neither transparent nor opaque to the probe light, but rather transmissive and absorbent to the probe light, and having a first end and a second end; inputting the analyte into the sensing channel; illuminating the analyte by coupling probe light at a sensing wavelength or range of wavelengths into the sensing channel through a first window formed in the tinted material integrally with the sensing channel and arranged adjacent the first end of the sensing channel; and detecting the probe light that has passed through the analyte by coupling the probe light out of the sensing channel through a second window formed in the tinted material integrally with the sensing channel and arranged adjacent the second end of the sensing channel.

We describe a low-cost high sensitivity opto-fluidic absorption cell for chemical and biochemical analysis manufactured from coloured materials.

We describe a technique for the manufacture of high sensitivity absorption cells from tinted or coloured polymers, in which microfluidic channels may be fabricated or may otherwise be manufactured. The principal action relates to very low levels of spurious scattered and/or reflected light entering the detector, and permits integrated spectral filtering, through the coloured/tinted polymer, over the length of the measurement cell. This method enables increased performance (sensitivity, S/N ratios, baseline noise and limit of detection) and simplifies manufacture leading to mass production at low-cost.

We now describe a cost effective and simple technique for the manufacture of such absorption cells. The opto-fluidic absorption cells are made using tinted or coloured substrates which absorb stray light from both the ambient and the source. Importantly, the substrates are not completely opaque allowing coupling of light in and out of the channel through thin semi-transparent optical windows, manufactured at either end of the absorption cell to couple the source and detector. This method simplifies manufacturing and avoids the requirement for insertion of transparent windows which would be required for totally opaque materials, and which would give dead volumes at the opto-fluidic junction. The optical absorption of the tinted substrate is a linear function of thickness so that there is a large ratio between absorption in the windows (typically 250 μm thick) and the absorption of stray light over the length of the optical cell (>10 mm).

The use of tinted polymer substrates has two further advantages:
1) the tint's spectral characteristics can be selected or tuned to a particular application; and
2) suitable polymer substrates are available as thick (up to 13 mm) sheets enabling integrated fluidic interconnections to be machined directly into the substrate.

The method can be applied to any tinted or coloured substrate using suitable microfabrication techniques.

The design, fabrication and characterisation of an opto-fluidic absorption cell system made by micromilling tinted PMMA is now described. The devices were first characterised using food dye, then evaluated using colourimetric assays for Iron and pH.

BRIEF DESCRIPTION OF THE DRAWINGS

The invention is now described by way of example with reference to the following drawings.

DETAILED DESCRIPTION

Material and Methods

Chip Fabrication

Figure 1:
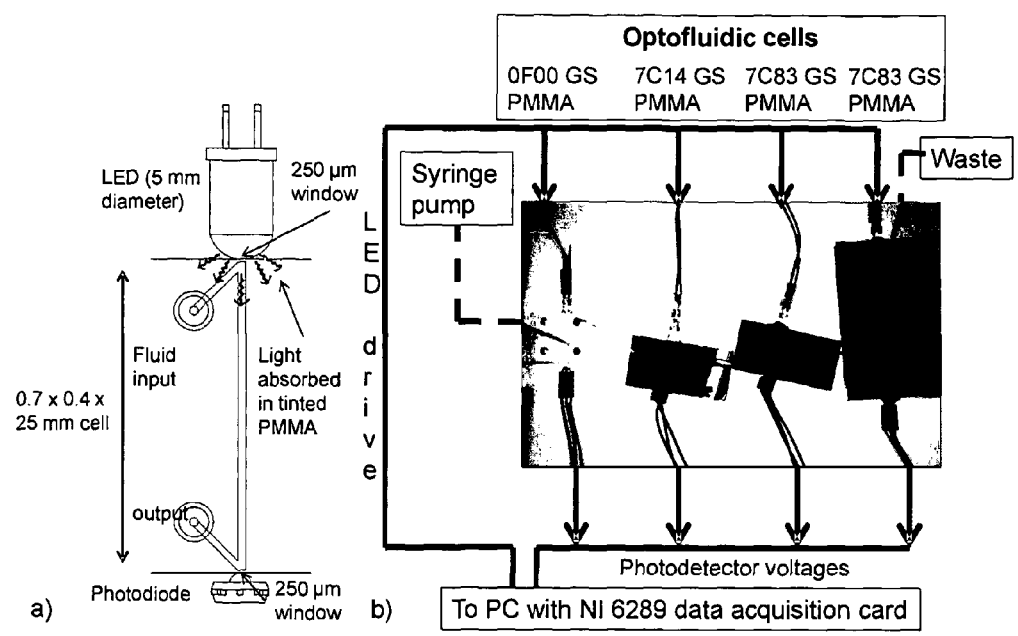
FIG. 1: (a) Schematic of an absorption cell with 250 μm thick windows. (b) Experimental setup for absorption cell evaluation. The four microfluidic cells (25 mm 0F00 GS, 25 mm 7C14 GS, 25 mm 7C83 GS and 80 mm 7C83 GS) are connected in series and a syringe pump is used to pump dye and samples premixed with reagent at 200 μl/min. A PC equipped with a NI 6289 data acquisition card was used to control the LEDs and acquire the data.

Opto-fluidic cells were micro-milled in different grades of PMMA, clear PMMA (0F00 GS, Röhm, Darmstadt, Germany), grey tint PMMA (7C14 GS, Röhm, Darmstadt, Germany) and dark tint PMMA (7C83 GS, Röhm, Darmstadt, Germany). Microfluidic channels, in this particular evaluation 700 µm wide and deep, but that which could be alternative channel sizes, were machined in PMMA sheets using a LPKF S100 Protomat micromill (LPKF laser and electronics AG, Garbsen, Germany), leaving windows of 250 µm thick in this case, but alternatively could be other similar dimensions, at either end of the channel. Fluidic connectors were cut in the body of the opto-fluidic cell. As a relatively thick (5 mm and more) PMMA substrate can be machined, standard fluidic connectors (¼" 28-UNF from Upchurch, or MINSTAC 062 from the Lee Co) can be used to interface the chip to macro-scale systems, thus removing the need for a dedicated interface and simplifying the manufacturing process. A lid of identical PMMA grade was aligned and solvent bonded[41] to close the opto-fluidic cells. Further details of the fabrication technique are described elsewhere[45]. The optical components were aligned with a homemade X Y Z stage and fixed in position with UV curable optical adhesive (Norland 68, NJ, USA). LEDs are used as light sources. For the iron assay, a LED centred on 562 nm (Stanley 5066X) was used, and for pH a custom made multi-wavelength LED (Roithner Laser-Technik GmbH, Austria) centred on the absorption peaks (435 nm, 592 nm) was used. A TAOS TSL257 photodiode (TAOS Inc., USA) was used to measure the light received at the end of the channel.

Two different absorption cell designs were made. The first design had an absorption channel of 25 mm length, manufactured in 8 mm thick clear transparent (0F00 GS), grey (7C14 GS) and dark tinted (7C83 GS) PMMA. The second design had an absorption channel 80 mm in length and was manufactured in 5 mm thick, dark tinted (7C83 GS) PMMA. The iron assay was performed in chips of both designs, the pH assay was performed using the longer path length chip.

Chemistry

All solutions were prepared with ultrapure water (18.2 MOhm.$cm^{-1}$ at 25 deg C.) from a Millipore water system (Milli-Q® system equipped with QPOD delivery unit).

Iron Experiment:

Dissolved iron was detected and quantified using Ferrozine (Aldrich) as described by Stookey[13] and Chin[42]. 1.25 g of Ferrozine was dissolved in 100 ml of 2 M acetic acid/sodium acetate buffer and diluted to 250 ml with ultrapure water. The 2 M buffer was prepared from 6.4 g of acetic acid (Sigma-Aldrich) and 155.3 g of acetate (Sigma-Aldrich) diluted to 1 L. A 20 mM stock solution of dissolved $Fe^{2+}$ was prepared by adding 0.7843 g of Ammonium ferrous sulphate (Sigma-Aldrich, 99.997%) in 100 ml of ultrapure water. To prevent oxidation to $Fe^{3+}$, the solution was stabilised by adding 100 µl of concentrated HCl (TraceSelectUltra, Sigma-Aldrich) and 100 µl of 1 mM sulfite solution (SigmaUltra). A working standard of 20 µM $Fe^{2+}$ was prepared and stabilised from the stock solution which was then used to generate a range of $Fe^{2+}$ standards (0 nM, 500 nM, 1 µM, 2 µM, 4 µM, 6 µM, 10 µM). All standards and reagents were kept in an air-tight bag in the dark and in a refrigerator at 4° C.

pH Experiment

A solution of $2 \times 10^{-3}$ M thymol blue (Sigma-Aldrich) was made following Zhang (Zhang et al, 1996). TRIS buffer (2-amino-2-hydroxy-1,3-propanediol) was prepared as described by Dickson[43]. For accurate determination of pH, the ratio of absorbance values at two wavelengths is required, together with temperature, salinity and thymol blue pKa values[44]. In this work only the absorbance values are measured in order to demonstrate the system's capability for high performance absorbance measurement at multiple wavelengths.

Analytic Procedures

The system set up is shown in FIG. 1. A range of calibration standards was prepared by mixing red food dye with Milli-Q water. Samples were injected into the opto-fluidic cells with a syringe pump (Harvard Apparatus Nanomite, Kent, UK) driving a 1000 µL Hamilton Gastight syringe (Nevada, USA) at a flow rate of 200 µL/min. A Milli-Q blank was run through the opto-fluidic cells between each prepared standard to monitor any baseline drift or possible contamination.

Freshly prepared Ferrozine was mixed with $Fe^{2+}$ standards (0 nM, 500 nM, 1 µM, 2 µM, 4 µM, 6 µM, 10 µM) at a 1:10 mixing ratio a few minutes before being injected in the opto-fluidic cells using the syringe pump (as above). The opto-fluidic cell was rinsed with 0.1 M HCl between each standard injection. A blank measurement was also recorded to enable compensation for any drift or contamination.

Data was recorded using a National Instruments Digital Acquisition Device PCI 6289 card with a sampling rate of 110 Hz and an anti-aliasing filter set at 10 Hz. Absorption and extinction coefficient values were calculated using the common logarithmic form of the Bouguer-Beer-Lambert law.

Reference spectra for the premixed food dye and iron standards with Ferrozine were obtained by use of a linear array photodiode spectrometer (HR4000, Ocean Optics) coupled to the same light sources used in the opto-fluidic cells. The absorption cell consisted of a 10 mm plastic cuvette for the food dye based measurements and a 100 mm glass cell for the iron assay. The cuvettes were rinsed with MilliQ and 0.1 M HCl in between each sample for the food dye standards and Iron standard respectively. Monochromatic measurements were obtained by selecting data from a single photodiode at a fixed wavelength (562 nm). Polychromatic measurements were obtained by integrating the intensity signals measured by the HR4000 over the full wavelength range.

pH data was acquired by serially adding 150 µL of $2\times10^{-3}$ M thymol blue to the TRIS buffer[44] and injecting it into the 80 mm absorption cell. Measurements were performed in an environmental chamber at a temperature of 25.0±0.1 deg C. The photodiode output was connected to a 16-bit analogue to digital converted controlled by a PIC microcontroller. As the photodiode cannot distinguish between the different wavelengths, each LED die was switched on independently (i.e. time division multiplexed).

PMMA absorbance spectra were obtained with a Hitachi U-28000 spectrophotometer (Hitachi, Japan) and normalised to account for the thickness of the PMMA sample.

Results and Discussion

Comparison of Different PMMA Samples

Figure 2:
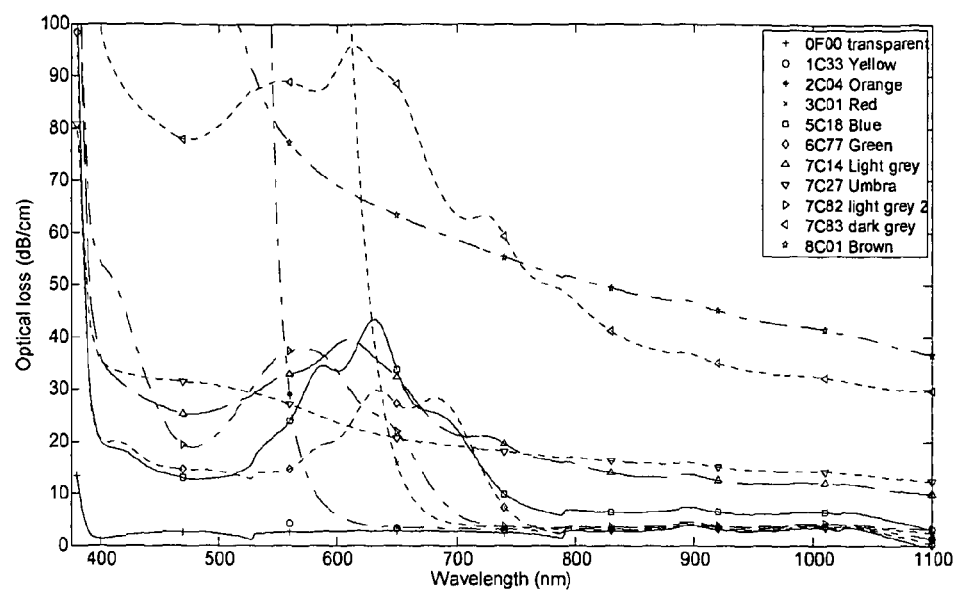
FIG. 2: Example absorbance spectra for some tinted and coloured transparent PMMA samples. The absorbance is represented in optical loss (dB/cm). The grey tint PMMA samples absorb light over a wide wavelength range, whereas some coloured PMMA samples (Yellow, Orange, Red and Blue) act as long pass filters. Inset: examples of commercially available coloured and tinted transparent PMMA (Rohm, Germany). Clockwise: 3C01 GS Red, 0F00 GS Transparent, 2C04 GS Orange, 7C14 GS Light grey, 5C18 GS Blue, and 1C33 GS Yellow.

The optical transmission of different commercially available PMMA samples were characterised, and the optical loss in dB/cm versus wavelength is shown in FIG. 2. Each sample (doping) has a different absorbance spectrum, so that they could be used as optical filters, (for a specific wavelength or a range of wavelengths, similar to neutral density filters). For example, 1C33 GS Yellow or 2C04 GS Orange PMMA provides light rejection for $\lambda<580$ nm, with good light transmission for $\lambda>600$ nm; both materials have optical losses higher than 100 dB/cm below 580 nm ($1\times10^{-8}$% transmission after 1 cm), better than 60% transmission above 600 nm. In designing the absorption cell, it is important to balance the thickness of the window, the path length, the optical power of the light source and the sensitivity of the photodetector. Table 1 summarises the optical losses for two different window thicknesses (100 µm and 250 µm) and absorption cell lengths (25 mm and 80 mm), at 560 nm.

TABLE 1

| Material | Window thickness (µm) | Cell length (mm) | Optical loss (dB/cm) at 560 nm | Transmission through window (%) | Transmission through cell length (%) | Transmission through 2 windows (%) |
|---|---|---|---|---|---|---|
| 0F00 GS Transparent | 250 | 25 | 2.5 | 98.6 | 23.7 | 97.2 |
| 7C14 GS Light grey | 250 | 25 | 32.9 | 82.7 | 6.0E−07 | 68.5 |
| 7C83 GS Dark grey | 250 | 25 | 88.9 | 59.9 | 6.0E−21 | 35.9 |
| 7C83 GS Dark grey | 250 | 80 | 88.9 | 59.9 | 7.6E−70 | 35.9 |
| 0F00 GS Transparent | 100 | 25 | 2.5 | 99.4 | 23.7 | 98.9 |
| 7C14 GS Light grey | 100 | 25 | 32.9 | 92.7 | 6.0E−07 | 85.9 |
| 7C83 GS Dark grey | 100 | 25 | 88.9 | 81.5 | 6.0E−21 | 66.4 |
| 7C83 GS Dark grey | 100 | 80 | 88.9 | 81.5 | 7.6E−70 | 66.4 |

Table 1 takes the measured optical loss values of three different PMMA samples of 3 mm thickness at 560 nm and calculates the expected light losses through the windows of the absorption cell. Results for two windows thicknesses (100 and 250 um) and cell lengths (25 and 80 mm) are presented. The worst stray light case is assumed by considering the shortest distance between the LED and the photodiode to be the length of the absorption cell (transmission through cell length in percent). In the case of the grey tint PMMAs (7C14 GS and 7C83 GS), only a negligible amount of stray light hits the photodetector after travelling in the PMMA, thus, minimising the deviation from linearity caused by the background light. The thinner the windows, the better the light transmission will be. However, thin windows will be less forgiving during the alignment phase of the chip fabrication. For absorption cells longer than 25 mm, the use of 7C14 GS as a material provides a good compromise in terms of light transmission, stray light rejection and windows thickness with 82.7% of the light transmitted through one 250 um window against 59.9% for 7C84 GS.

Total internal reflection (TIR) can and does occur at the substrate—air interface. Therefore, in clear substrates an appreciable background signal consisting of light directly transmitted through the substrate and internally reflected light is measured by the detector. The TIR signal has a longer path-length than the direct illumination path, and therefore the use of the geometric cell length in the calculation of background suppression (in table 1) is an underestimate. If the optical power from the light source is the limiting factor, the choice of material and the thickness of the window will have a major impact: less than 40% or 70% of the light is transmitted through the optical windows (250 μm and 100 μm respectively) made from 7C83 GS Dark grey PMMA against 70% and 85% (250 μm and 100 μm windows respectively) for 7C14 GS Light Grey PMMA.

Figure 3A:
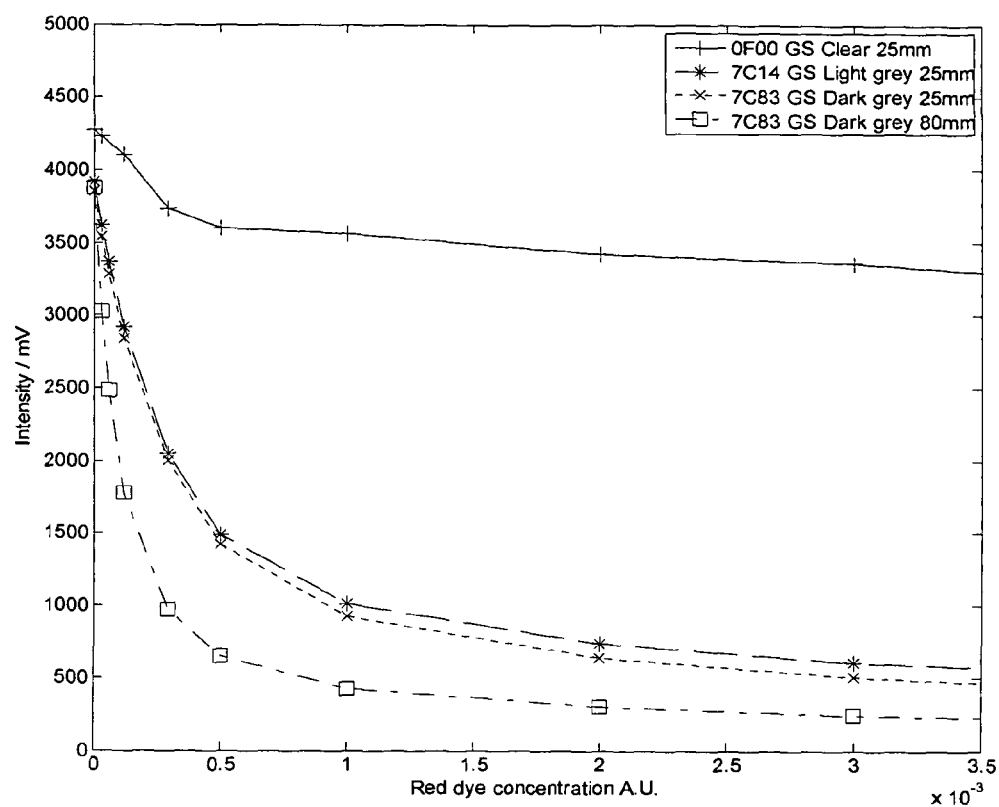
FIG. 3: Graphs comparing the optical performance of absorption channels constructed in different tinted PMMA substrates using red food dye as the sample. (a) shows the variation of measured optical intensity (mV) as a function of dye concentration (AU) for 25 mm cells in clear, grey and dark grey tinted PMMA and also for an 80 mm cell constructed in dark grey tinted PMMA. This illustrates that the background intensity is greatly reduced using tinted substrates, and that the longer cell has greater sensitivity. In each instance the LED drive current is adjusted to give a similar optical intensity when measuring a blank sample. (b) shows the absorption calculated from intensity data shown in a) above compared with measurements using a reference spectrometer (HR4000 Ocean Optics). The darker PMMA tints reduce background light and hence enhance sensitivity (by up to a factor 6). The measurement range is also improved.
Figure 3B:
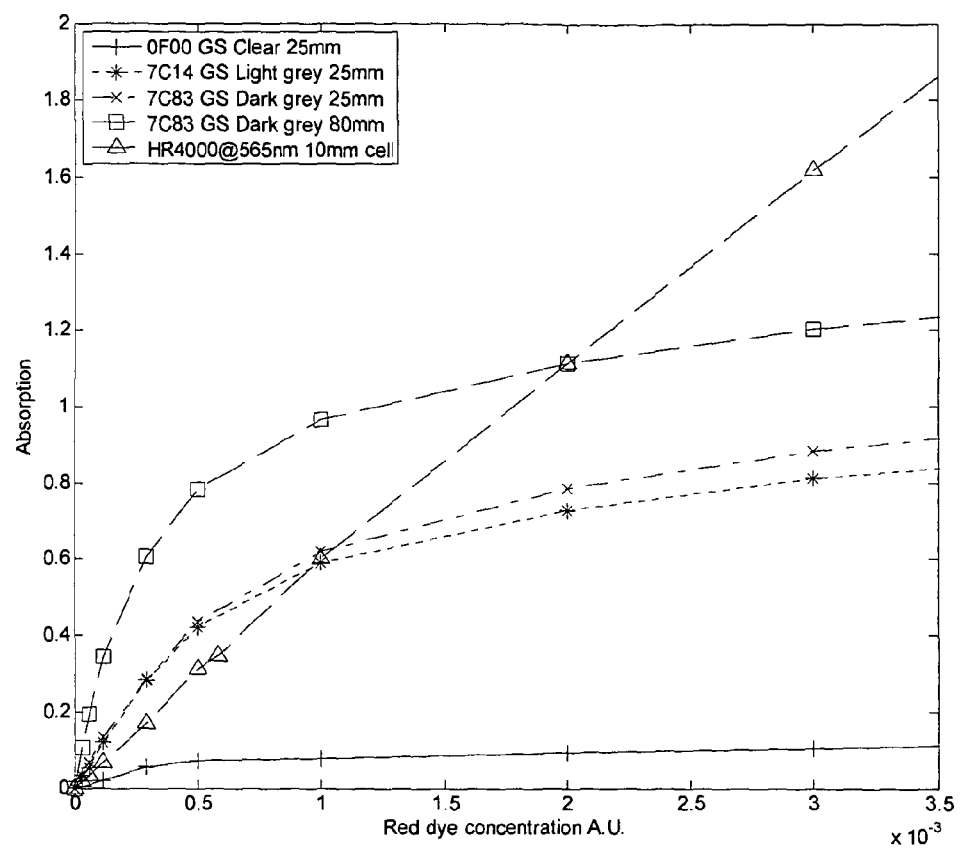
Figure 4:
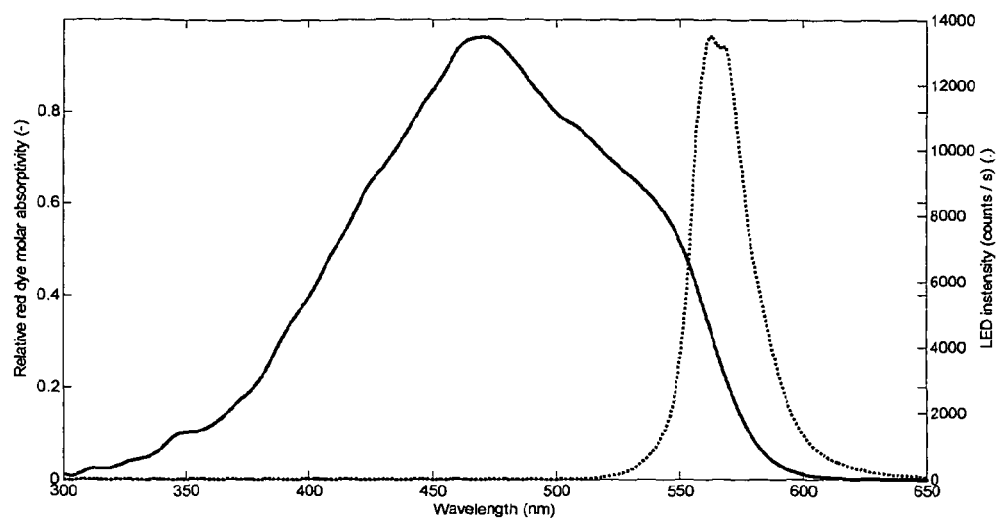
FIG. 4: Graph showing spectral variation of the molar absorption coefficient for the red dye and LED spectrum. The LED optical output spectrum is not centred on the red dye absorption peak (562 nm and 470 nm respectively) and part of the LED intensity will not be absorbed by the dye. As a consequence, the background intensity seen by the photodiode will be high, and as shown in Equation 5, incorrect application of the Bouguer-Beer-Lambert law will result in a non linear relationship between concentration and absorption. This is the typical case described by Galli[24].

FIG. 3(a) shows the effect of the PMMA doping density on the stray light in the opto-fluidic absorption cells. FIG. 3(b) illustrates the effect of neglecting stray light and, assuming monochromatic illumination in application of the Bouguer-Beer-Lambert law (Equation 5) and the improvement observed using tinted absorption cells. When using clear transparent PMMA (0F00 GS) as a substrate and red food dye as an analyte, the background measured by the photodiode is high (FIG. 3(a)). When this data is used without compensation to calculate absorption (FIG. 3(b)) a rapid deviation from linearity and a drastically reduced sensitivity results: a maximum absorption value of 0.16 is obtained whereas the true value is ~4.5 (~1.8/cm). The nonlinearity shown in FIG. 3(b) is due to the combined effects of stray light and the use of a polychromatic source that is not matched to the absorption spectrum of the dye (see FIG. 4). The use of tinted PMMA improved the sensitivity, particularly at low dye concentrations (up to a factor 6) and also increased the measurement range. Transparent PMMA allows good light transmission but increases the stray light, leading to a high background measurement. The emission angle from the light source is much wider than the channel and not collimated, thus a large amount of the emitted light is not absorbed by the liquid in the channel. Additionally, the high refractive index of PMMA (around 1.55) compared to air or water (~1.00 and 1.33 respectively) promotes total internal reflection (TIR), meaning that unwanted non-collimated light is incident on the photodetector giving a high background. This leads to a reduced measuring range, deviation from linearity (without compensation of the Bouguer-Beer-Lambert law) and poor limit of detection. The use of tinted or coloured transparent PMMA alleviates these problems.

Detection of Iron and pH

Figure 5A:
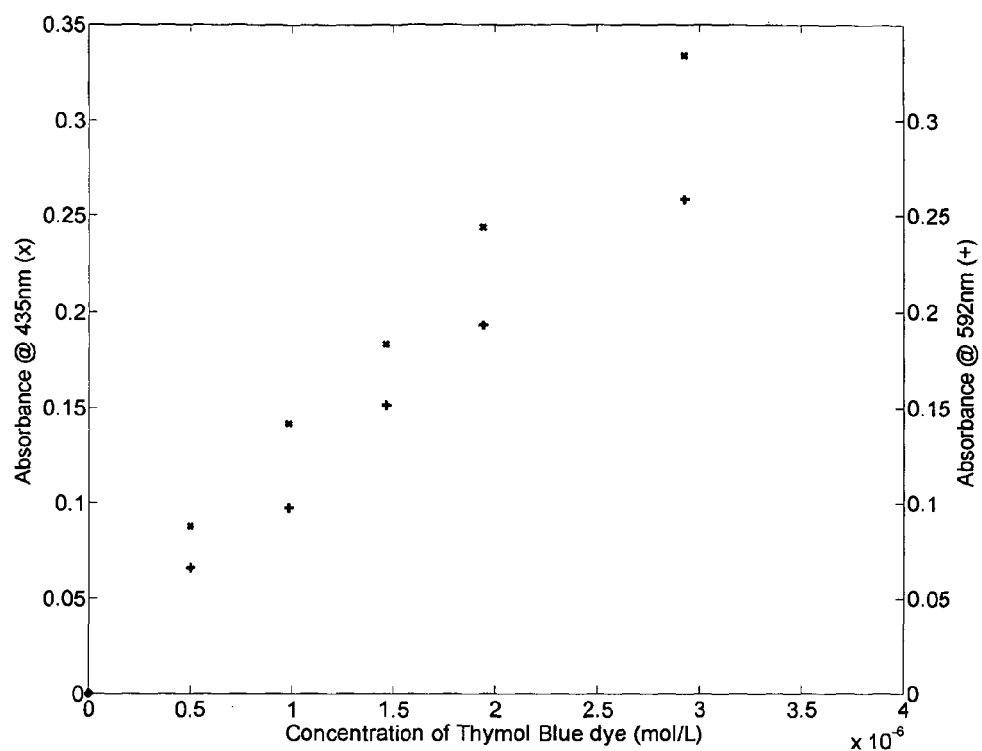
FIG. 5: Graphs showing absorption versus concentration for two example applications (pH (a) and iron (b) in water). (a) shows the variation in absorption of thymol blue as its concentration increases at two distinct wavelengths (435 nm and 592 nm) measured with an 80 mm absorption cell fabricated in dark tinted PMMA. This demonstrates the use of the method for a multi-wavelength assay. (b) compares the results obtained with the opto-fluidic absorption cells to measurements made using a bench-top spectrometer (Ocean Optics HR4000). Each point is the average of a triplicate measurement with the associated error bar ($1\sigma$). The effective molar absorption coefficient was calculated for all the PMMA chips and compared to the theoretical value (27,900 $cm^{-1}$ at 562 nm)[13] in ideal conditions. For the clear transparent PMMA (0F00 GS), the effective molar absorption coefficient was 3,718 $cm^{-1}$, 21,520 $cm^{-1}$ for 7C14 GS (Light grey), 23,160 $cm^{-1}$ for 7C83 GS (Dark grey). The use of tinted PMMA improved the sensitivity of the system by a factor 6.2. The LOD is improved because of the reduced background illumination. The LOD was 124 nM, 50 nM, and 34 nM for the 25 mm long absorbance cell made of 0F00 GS, 7C14 GS, and 7C83 GS respectively.

Colourimetric assays for $Fe^{2+}$ and pH were performed to demonstrate the benefits of the tinted material technique over the use of clear transparent substrate. In both instances the output spectra of the LEDs used as light sources are well matched (e.g. Ferrozine absorption peak centred on 562 nm with a full width half maximum (FWHM) of ~100 nm and a LED emission peak centred on 562 nm with a FWHM ~30 nm for the $Fe^{2+}$ assay) to the absorption spectra of the assay's coloured products resulting in improved linearity when applying the Bouguer-Beer-Lambert law without compensation for stray light or polychromatic effects. FIG. 5(a) shows that the technique can be used for multi-wavelength analysis. The absorbance at 435 nm and 592 nm of TRIS buffer mixed with thymol blue was measured for an 80 mm long opto-fluidic cell. Good linearity was observed and the limit of detection (LOD), expressed as three times the standard deviation of the blank measurement was $2.2 \times 10^{-4}$ absorption units at 435 nm, and $9.4 \times 10^{-4}$ absorption units at 592 nm, with 10 s signal averaging.

Figure 5B:
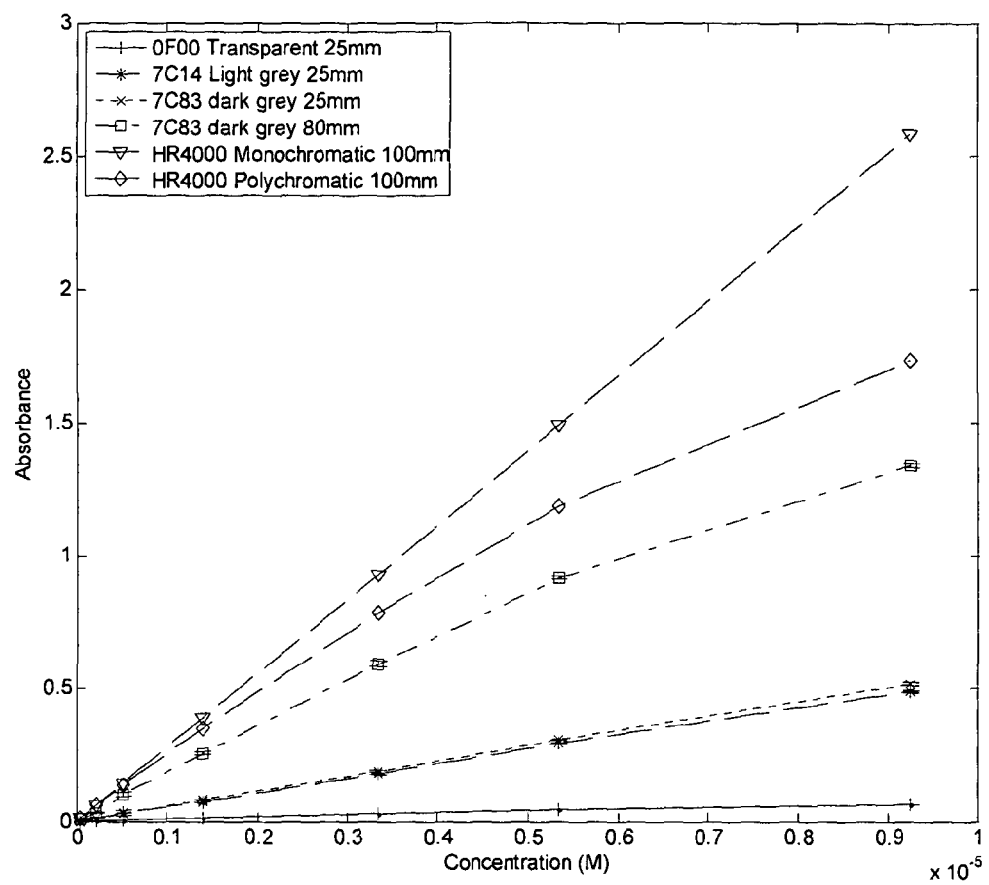

Results from the $Fe^{2+}$ colourimetric assay are summarised in FIG. 5(b). Data are compared to the HR4000 spectrometer for the monochromatic and polychromatic cases. As a measure of sensitivity, the equivalent molar absorption coefficient was calculated for all the PMMA opto-fluidic cells and compared to the theoretical value (27,900 $cm^{-1}$ at 562 nm)[13] by calculating the slope of each curve in the linear region. This approximation gives a figure of merit representative of the performances of the system. For the clear transparent PMMA (0F00 GS), the molar absorption coefficient was 3,718 $cm^{-1}$; 21,520 $cm^{-1}$ for 7C14 GS (Light grey) and 23,160 $cm^{-1}$ for 7C83 GS (Dark grey). The use of tinted PMMA improved the sensitivity of the system by a factor 6.2. The LOD also improved from the reduced background illumination. The LOD was 124 nM; 50 nM; and 34 nM for 0F00 GS, 7C14 GS, and 7C83 GS respectively (25 mm long absorbance). The use of a longer absorbance cell did not improve the LOD significantly (33 nM), most likely due to quality of the blank sample. At such low levels, an iron-free cleanroom environment is necessary to prepare precise samples and avoid contamination. The small deviation from linearity observed when applying the Bouguer-Beer-Lambert law without compensation is caused by the polychromatic light source. The deviation is smaller than observed when using dye, because the LED output spectrum is more closely matched to the absorption spectrum of the chromophore. Using integration of spectrometer (HR4000) light intensity data over the wavelength range of the source to calculate absorption (i.e. the polychromatic case) and normalising the curve obtained for an 80 mm absorption cell length, yields good agreement with absorption measurements using the 80 mm long 7C83 GS dark grey PMMA cell. A correlation factor of 0.96 is calculated (with $R^2 = 0.9996$). Contrary to the HR400 photodiode array, the TAOS TSL257 sensitivity is not linearised over its wavelength range, this could account for the difference in measured absorbance.

Conclusion

We have demonstrated a generic low-cost, technique for the manufacture of high performance opto-fluidic systems. The use of a coloured/tinted material to manufacture optical cells with built-in windows reduces the microfluidic chip dead volume, improves the linearity of the system (for absorbance measurements) and increases the sensitivity by a factor 6 (minimum) when compared to clear transparent material. The technique allows for robust long path-length absorption cells to be manufactured, obviates the need for fibre optic coupling of sources or detectors, and can potentially be extended to any material with an optical doping capability. On chip microlenses with integrated filter could also be manufactured using this technique.

We describe a cost-effective and simple technique for the manufacture of high sensitivity absorption cells for microfluidic chemical analytical systems. The chips are made from tinted or coloured polymers, for example polymethylmethacrylate (PMMA) in which microfluidic channels are cut. Light is coupled into the absorption cell via two windows (typically 200 um thick) that are retained at either end of the channel. Absorption is measured using an LED and a photodiode butted against the windows. Spurious scattered and/or reflected light is absorbed by the coloured polymer over the length of the measurement cell, while very little light loss occurs at the coupling windows. Compared with conventional transparent materials, the coloured polymers demonstrate increased performance figures (sensitivity, S/N ratios, baseline noise and limit of detection). Absorption cells of 25 mm and 80 mm path length, with cross section 700 um×400 um were manufactured from different grades of tinted PMMA. Their performances were compared to chips made of clear PMMA. Tinted PMMA devices had sensitivities and measuring ranges 6 times greater than clear PMMA. The microfluidic chips could be made from any coloured or tinted material.

Normally transparent materials can be modified by the addition of dyes tailored to meet specific optical requirements.

REFERENCES

1. A. Manz, N. Graber and H. M. Widmer, *Sensors and Actuators B-Chemical*, 1990, 1, 244-248.
2. P. S. Dittrich, K. Tachikawa and A. Manz, *Anal. Chem.*, 2006, 78, 3887-3908.
3. H. F. Li and J. M. Lin, *Anal. Bioanal. Chem.*, 2009, 393, 555-567.
4. L. Marie and G. M. Greenway, *Trac-Trends Anal. Chem.*, 2005, 24, 795-802.
5. R. R. Hood, K. E. Kohler, J. P. McCreary and S. L. Smith, *Deep-Sea Res. Part II-Top. Stud. Oceanogr.*, 2003, 50, 2917-2945.
6. M. A. M. Friedrichs, J. A. Dusenberry, L. A. Anderson, R. A. Armstrong, F. Chai, J. R. Christian, S. C. Doney, J. Dunne, M. Fujii, R. Hood, D. J. McGillicuddy, J. K. Moore, M. Schartau, Y. H. Spitz and J. D. Wiggert, *J. Geophys. Res.-Oceans*, 2007, 112, 22.
7. H. W. Ducklow, S. C. Doney and D. K. Steinberg, *Annu. Rev. Mar. Sci.*, 2009, 1, 279-302.
8. P. Brasseur, N. Gruber, R. Barciela, K. Brander, M. Doron, A. El Moussaoui, A. J. Hobday, M. Huret, A. S. Kremeur, P. Lehodey, R. Matear, C. Moulin, R. Murtugudde, I. Senina and E. Svendsen, *Oceanography*, 2009, 22, 206-215.
9. T. L. Delworth, A. J. Broccoli, A. Rosati, R. J. Stouffer, V. Balaji, J. A. Beesley, W. F. Cooke, K. W. Dixon, J. Dunne, K. A. Dunne, J. W. Durachta, K. L. Findell, P. Ginoux, A. Gnanadesikan, C. T. Gordon, S. M. Griffies, R. Gudgel, M. J. Harrison, I. M. Held, R. S. Hemler, L. W. Horowitz, S. A. Klein, T. R. Knutson, P. J. Kushner, A. R. Langenhorst, H. C. Lee, S. J. Lin, J. Lu, S. L. Malyshev, P. C. D. Milly, V. Ramaswamy, J. Russell, M. D. Schwarzkopf, E. Shevliakova, J. J. Sirutis, M. J. Spelman, W. F. Stern, M. Winton, A. T. Wittenberg, B. Wyman, F. Zeng and R. Zhang, *J. Clim.*, 2006, 19, 643-674.
10. K. S. Johnson, W. M. Berelson, E. S. Boss, Z. Chase, H. Claustre, S. R. Emerson, N. Gruber, A. Kortzinger, M. J. Perry and S. C. Riser, *Oceanography*, 2009, 22, 216-225.
11. P. Griess, *Berichte der deutschen chemischen Gesellschaft*, 1879, 12, 426-428.
12. W. R. G. Atkins, *Journal of the Marine Biological Association of the United Kingdom*, 1923, 13, 119-150.
13. L. L. Stookey, *Anal. Chem.*, 1970, 42, 779-&.
14. C. S. Chin, K. S. Johnson and K. H. Coale, *Marine Chemistry*, 1992, 37, 65-82.
15. K. Grasshoff, K. Kremling and M. Ehrhardt, *Methods of Seawater Analysis (Third Edition)*, Wiley-VCH, Weinheim (Federal Republic of Germany), 1999.
16. F. A. J. Armstrong, C. R. Stearns and J. D. H. Strickland, *Deep Sea Res*, 1967, 14, 381-389.
17. A. K. Hanson, OCEANS 2000 MTS/IEEE Conference and Exhibition, 2000.
18. D. Thouron, R. Vuillemin, X. Philippon, A. Lourenco, C. Provost, A. Cruzado and V. Garcon, *Anal. Chem.*, 2003, 75, 2601-2609.
19. L. R. Adornato, E. A. Kaltenbacher, T. A. Villareal and R. H. Byrne, *Deep Sea Research Part I: Oceanographic Research Papers*, 2005, 52, 543-551.
20. M. D. Patey, M. J. A. Rijkenberg, P. J. Statham, M. C. Stinchcombe, E. P. Achterberg and M. Mowlem, *Trac-Trends Anal. Chem.*, 2008, 27, 169-182.
21. Bouguer, *Essai d'optique sur la gradation de la lumiere*, A Paris: Chez Claude Jombert . . . 1729.
22. J. H. Lambert, *I. H. Lambert Photometria, sive, De mensura et gradibus luminis, colorum et umbrae [microform]*, V. E. Klett, Augustae Vindelicorum: 1760.
23. Beer, *Annalen der Physik*, 1852, 162, 78-88.
24. C. Galli, *Journal of Pharmaceutical and Biomedical Analysis*, 2001, 25, 803-809.
25. H. C. Hunt and J. S. Wilkinson, *Microfluid. Nanofluid.*, 2008, 4, 53-79.
26. B. Kuswandi, Nuriman, J. Huskens and W. Verboom, *Anal. Chim. Acta*, 2007, 601, 141-155.
27. Z. H. Liang, N. Chiem, G. Ocvirk, T. Tang, K. Fluri and D. J. Harrison, *Anal. Chem.*, 1996, 68, 1040-1046.
28. G. M. Greenway, S. J. Haswell and P. H. Petsul, *Anal. Chim. Acta*, 1999, 387, 1-10.
29. M. Grumann, J. Steigert, L. Riegger, I. Moser, B. Enderle, K. Riebeseel, G. Urban, R. Zengerle and J. Ducree, *Biomed. Microdevices*, 2006, 8, 209-214.
30. K. W. Ro, K. Lim, B. C. Shim and J. H. Hahn, *Anal. Chem.*, 2005, 77, 5160-5166.
31. A. Datta, I. Y. Eom, A. Dhar, P. Kuban, R. Manor, I. Ahmad, S. Gangopadhyay, T. Dallas, M. Holtz, F. Temkin and P. K. Dasgupta, *IEEE Sens. J.*, 2003, 3, 788-795.
32. W.-B. Du, Q. Fang, Q.-H. He and Z.-L. Fang, *Anal. Chem.*, 2005, 77, 13304337.
33. M. P. Duggan, T. McCreedy and J. W. Aylott, *Analyst*, 2003, 128, 1336-1340.
34. R. Manor, A. Datta, I. Ahmad, M. Holtz, S. Gangopadhyay and T. Dallas, *IEEE Sens. J.*, 2003, 3, 687-692.
35. H. Salimi-Moosavi, Y. T. Jiang, L. Lester, G. McKinnon and D. J. Harrison, *Electrophoresis*, 2000, 21, 1291-1299.
36. L. Billot, A. Plecis and Y. Chen, *Microelectron. Eng.*, 2008, 85, 1269-1271.
37. K. A. Remley and A. Weisshaar, *Opt. Lett.*, 1996, 21, 1241-1243.
38. G. Pandraud, T. M. Koster, C. Gui, M. Dijkstra, A. van den Berg and P. V. Lambeck, *Sens. Actuator A-Phys.*, 2000, 85, 158-162.
39. O. Hofmann, X. H. Wang, A. Cornwell, S. Beecher, A. Raja, D. D. C. Bradley, A. J. deMello and J. C. deMello, *Lab Chip*, 2006, 6, 981-987.
40. C. L. Bliss, J. N. McMullin and C. J. Backhouse, *Lab Chip*, 2008, 8, 143-151.
41. C. W. Tsao and D. L. DeVoe, *Microfluid. Nanofluid.*, 2009, 6, 1-16.
42. C. S. Chin, K. H. Coale, V. A. Elrod, K. S. Johnson, G. J. Massoth and E. T. Baker, *J. Geophys. Res.-Solid Earth*, 1994, 99, 4969-4984.
43. A. G. Dickson, Sabine C. L., Christian J. R., *PICES Special Publication*, 2007, 3, 191.
44. H. N. Zhang and R. H. Byrne, *Marine Chemistry*, 1996, 52, 17-25.
45. I. R. G. Ogilvie, V. J. Sieben, C. F. A. Floquet, R. Zmijan, M. C. Mowlem, *J. Micromech. Microeng*, 2010, 20, 1-8.

The invention claimed is:

1. An absorption cell for measuring absorption of a fluid analyte at a sensing wavelength, or range of sensing wavelengths, by exposing the analyte to probe light of the sensing wavelength or sensing wavelength range, the absorption cell comprising:
   a microfluidic sensing channel having first and second ends so as to provide a fluid path for the analyte as well as an optical path for the probe light;
   first and second windows adjacent the first and second ends of the sensing channel which are transmissive to the probe light;

wherein
the sensing channel is formed in a tinted material which is neither transparent nor opaque to the probe light, but rather transmissive and absorbent to the probe light, and in that the first and second windows are formed in the same tinted material integrally with the sensing channel.

2. The absorption cell of claim 1, wherein the tinted material has an optical loss to the probe light of between 10 to 90 dB/cm.

3. The absorption cell of claim 1, wherein the length of the sensing channel is at least 10 mm.

4. The absorption cell of claim 1, wherein the ratio of the length of the sensing channel to the combined thickness of the first and second windows is greater than or equal to 50.

5. The absorption cell of claim 1, wherein the transmission of the probe light in the tinted material over a path length equal to the combined thickness of the first and second windows is between 30% and 90%.

6. The absorption cell of claim 1, wherein the transmission of the probe light in the tinted material over a path length equal to the length of the sensing channel is less than $10^{-8}$.

7. The absorption cell of claim 1, wherein the ratio of the transmission of the probe light in the tinted material over a path length equal to the combined thickness of the first and second windows, and the transmission of the probe light in the tinted material over a path length equal to the length of the sensing channel is at least $10^8$.

8. The absorption cell of claim 1, wherein the sensing channel is connected at its first end by a first elbow to a microfluidic input channel in fluid communication with a fluid input and at its second end by a second elbow to a microfluidic output channel in fluid communication with a fluid output.

9. The absorption cell of claim 8, wherein the first and second windows have first and second internal faces formed at the first and second elbows between the first and second ends of the sensing channel and the input and output channel respectively, and first and second external faces through which probe light is able to couple into and out of the absorption cell respectively.

10. An absorption cell device for measuring absorption of a fluid analyte at a sensing wavelength, or range of sensing wavelengths, by exposing the analyte to probe light of the sensing wavelength or sensing wavelength range, the device comprising:
a microfluidic input channel in fluid communication with a fluid input;
a microfluidic output channel in fluid communication with a fluid output;
a microfluidic sensing channel having first and second ends in fluid connection with the input channel and output channel respectively, so as to provide a fluid path for the analyte as well as an optical path for the probe light;
first and second windows adjacent the first and second ends of the sensing channel which are transmissive to the probe light;
a light source operable to generate the probe light and arranged to direct the probe light into the optical path through the first window; and
a photodetector operable to sense the probe light and arranged to receive the probe light from the optical path through the second window,
wherein
the sensing channel is formed in a tinted material which is neither transparent nor opaque to the probe light, but rather transmissive and absorbent to the probe light, and in that the first and second windows are formed in the same tinted material integrally with the sensing channel.

11. The device of claim 10, wherein the first and second windows have first and second internal faces formed at first and second channel elbows between the first and second ends of the sensing channel and the input and output channel respectively, and first and second external faces through which probe light is able to couple into and out of the absorption cell respectively.

12. A method of performing an absorption measurement of a fluid analyte, the method comprising:
providing an absorption cell with a microfluidic sensing channel having a first end and a second end;
inputting the analyte into the sensing channel;
illuminating the analyte by coupling probe light at a sensing wavelength or range of wavelengths into the sensing channel through a first window adjacent the first end of the sensing channel; and
detecting the probe light that has passed through the analyte by coupling the probe light out of the sensing channel through a second window adjacent the second end of the sensing channel, wherein the sensing channel is formed in a tinted material which is neither transparent nor opaque to the probe light, but rather transmissive and absorbent to the probe light, and in that the first and second windows are formed in the same tinted material integrally with the sensing channel.

* * * * *